United States Patent
Sievert

(10) Patent No.: US 8,053,613 B2
(45) Date of Patent: Nov. 8, 2011

(54) PROCESSES FOR PRODUCING 1,2,3,3,3-PENTAFLUOROPROPENE AND PRECURSORS THEREOF

(75) Inventor: Allen Capron Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 342 days.

(21) Appl. No.: 12/377,761

(22) PCT Filed: Sep. 5, 2007

(86) PCT No.: PCT/US2007/019317
§ 371 (c)(1),
(2), (4) Date: Feb. 17, 2009

(87) PCT Pub. No.: WO2008/030442
PCT Pub. Date: Mar. 13, 2008

(65) Prior Publication Data
US 2010/0197981 A1   Aug. 5, 2010

Related U.S. Application Data

(60) Provisional application No. 60/842,609, filed on Sep. 5, 2006.

(51) Int. Cl.
*C07C 19/08* (2006.01)
(52) U.S. Cl. ........ 570/170; 570/155; 570/156; 570/160; 570/167
(58) Field of Classification Search .......... None
See application file for complete search history.

(56) References Cited

U.S. PATENT DOCUMENTS

| | | | |
|---|---|---|---|
| 5,157,171 A | 10/1992 | Sievert et al. | |
| 5,177,274 A * | 1/1993 | Aoyama et al. | 570/172 |
| 5,264,639 A * | 11/1993 | Morikawa et al. | 570/168 |
| 5,396,000 A | 3/1995 | Nappa et al. | |
| 5,488,189 A | 1/1996 | Sievert et al. | |
| 6,184,426 B1 * | 2/2001 | Belen'Kill et al. | 570/172 |
| 6,369,284 B1 * | 4/2002 | Nappa et al. | 570/156 |

FOREIGN PATENT DOCUMENTS

| | | |
|---|---|---|
| WO | 98/33755 | 8/1998 |
| WO | 98/42645 | 10/1998 |
| WO | 2008030438 | 3/2008 |
| WO | 2008030439 | 3/2008 |
| WO | 2008030441 | 3/2008 |
| WO | 2008054778 | 5/2008 |

OTHER PUBLICATIONS

G.G. Belen'KII et al: "Electrophilic Catalytic Alkylation of Polyfluoroolefins by Some Fluoroalkanes", Journal of Fluorine Chemistry, Elsevier Sequoia, Lausanne, CH., vol. 108, No. 1, Mar. 2001, p. 15-20.

* cited by examiner

*Primary Examiner* — Sudhakar Katakam

(57) ABSTRACT

A process is disclosed for making $CH_2ClCF_2CClF_2$. The process involves reacting $CH_2ClF$ with $CClF=CF_2$ in an addition reaction zone in the presence of an aluminum halide composition having a bulk formula of $AlCl_xBr_yF_{3-x-y}$ wherein the average value of x is 0 to 3, the average value of y is 0 to 3−x, provided that the average values of x and y are not both 0. Also disclosed is a process for making $CH_2FCF_2CF_3$ that involves reacting the $CH_2ClCF_2CClF_2$ with HF in a fluorination reaction zone in the presence of a fluorination catalyst. Also disclosed is a process for making $CHF=CFCF_3$ that involves dehydrofluorinating the $CH_2FCF_2CF_3$.

5 Claims, No Drawings

US 8,053,613 B2

PROCESSES FOR PRODUCING 1,2,3,3,3-PENTAFLUOROPROPENE AND PRECURSORS THEREOF

FIELD OF THE INVENTION

The present invention relates to processes that involve the production of 1,2,3,3,3-pentafluoropropene and precursors thereof (e.g., 1,3-dichloro-1,1,2,2-tetrafluoropropane and/or 1,1,1,2,2,3-hexafluoropropane).

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFC-1225ye, having zero ozone depletion and a low global warming potential, has been identified as a potential refrigerant. U.S. Pat. No. 5,396,000 discloses a process for producing HFC-1225ye by dehydrofluorination of $CF_3CFHCF_2H$ (HFC-236ea). There is a need for new manufacturing processes for the production of HFC-1225ye.

SUMMARY OF THE INVENTION

The present invention provides a process for making $CH_2ClCF_2CClF_2$ (HCFC-234cc). The process comprises reacting $CH_2ClF$ (HCFC-31) with $CClF=CF_2$ (CTFE) in a reaction zone in the presence of a catalytically effective amount of an aluminum halide composition having a bulk formula of $AlCl_xBr_yF_{3-x-y}$, wherein the average value of x is 0 to 3, the average value of y is 0 to 3−x, provided that the average values of x and y are not both 0.

The present invention also provides a process for making $CH_2CF_2CF_3$ (HFC-236cb). The process comprises reacting HCFC-234cc produced by the above process with HF in a reaction zone in the presence of a fluorination catalyst to produce a product comprising HFC-236cb.

The present invention also provides a process for making $CHF=CFCF_3$ (HFC-1225ye). The process comprises dehydrofluorinating HFC-236cb produced by the above process to form HFC-1225ye.

DETAILED DESCRIPTION

The present invention provides a process for making HCFC-234cc. The process comprises reacting $CH_2ClF$ (HCFC-31) with $CClF=CF_2$ (CTFE) in a reaction zone in the presence of an aluminum halide composition having a bulk formula of $AlCl_xBr_yF_{3-x-y}$, wherein the average value of x is 0 to 3, the average value of y is 0 to 3−x, provided that average values of x and y are not both 0. Of note are embodiments wherein x is from about 0.10 to 3.00 and y is 0. Aluminum halide compositions of this type are known; see U.S. Pat. Nos. 5,157,171 and 5,162,594. In some cases HCFC-31 may be employed in the formation of the aluminum halide composition. Thus, in some embodiments, use of sufficient excess of HCFC-31 enables the production of $AlCl_xF_{3-x}$ in situ from anhydrous aluminum chloride so that a fluorine-containing catalyst is obtained.

The addition reaction involving HCFC-31 and CTFE is based on a stoichiometry of 1 mole of HCFC-31 per mole of CTFE. However, an excess of either reactant may be used as desired. An excess of HCFC-31 may reduce cycloaddition of CTFE with itself. An excess of CTFE may promote CTFE-based by-products such as the cycloaddition reaction products and/or the formation of five carbon products. Typically, the mole ratio of CTFE to HCFC-31 is about 1.5 or less (e.g., from about 0.3:1 to about 1.1:1).

The process can be conducted batchwise or in a continuous manner. In the continuous mode, a mixture of HCFC-31 and CTFE may be passed through or over a bed or body of the aluminum halide composition (which may be under agitation) at suitable temperature and pressure to form a product stream, and the desired products (e.g., HCFC-234cc) may be recovered from the stream by conventional methods such as fractional distillation.

In the batch process, the reactants and the aluminum halide composition may be combined in a suitable reactor to form a reaction mixture, and the mixture held at a suitable temperature and pressure (normally under agitation) until a desired degree of conversion is obtained. In one embodiment, the reactor is initially charged with the aluminum halide composition, and optionally with a diluent, then the HCFC-31 and CTFE are fed in the desired mole ratio (as separate streams or as a combined stream) into the reactor and maintained therein until the reaction is substantially complete. If the reactor is fed with HCFC-31 and the aluminum halide composition are fed to the reactor in the substantial absence of the CTFE, then reactor and ingredients should be kept relatively cold (e.g., between about −78° C. and 10° C.) to discourage disproportionation of the HCFC-31 to methanes having different fluorine content.

The process may be practiced with or without a solvent or diluent for the HCFC-31 and CTFE. Typically, the HCFC-31 and CTFE are diluted; however, the diluent may be primarily the HCFC-234 produced in the addition reaction. Solvents which may be used include $CH_2Cl_2$, $CHCl_3$, $CCl_4$, $CHCl_2CF_3$, $CClF_2CClF_2$, and cyclo-$C_4Cl_2F_6$ and mixtures thereof.

The addition reaction zone temperature is typically in the range of from about 0° C. to about 100° C. Of note are embodiments wherein the addition reaction zone temperature is in the range of from about 20° C. to about 80° C.

The reaction pressure may vary widely but normally the reaction is carried out at elevated pressures, particularly pressures generated autogeneously in conformity with the reaction temperature employed. The pressure may be adjusted by controlling the amount of unreacted HCFC-31 and CTFE.

At normally employed temperatures, the reaction time is typically between about 0.2 hour and 12 hours.

The amount of aluminum halide composition employed is typically in the range of from about one to twenty percent by weight based on the weight of the HCFC-31 reactant.

The effluent from the reaction zone (continuous or batch) typically includes HCFC-234cc, unreacted HCFC-31 and/or CTFE, and other HCFC-234 isomers having the formula $CH_2XCFXCX_2F$ (wherein two X are Cl and the other two X are F). The effluent may also include one or more other by-products such as $CH_2Cl_2$ and cyclo-$C_4Cl_2F_6$ isomers. It has been found in accordance with this invention that the HCFC-234cc isomer can be produced with high selectivity (about 50 mole % or more of three-carbon addition products).

The reaction products may be recovered from the reaction zone by use of a suitable conventional means such as by filtration and/or distillation. In batch mode, it is normally convenient to separate the reaction products from the aluminum halide composition and to use the separated aluminum halide composition in subsequent batches.

The HCFC-234cc produced by the addition reaction as described above can be used to produce HFC-236cb by catalytic fluorination.

In one embodiment the HCFC-234cc is separated from the effluent from the addition reaction zone. In another embodiment HCFC-234cc and other compounds of the formula $CH_2XCFXCX_2F$, wherein two X are Cl and the other two X are F that are present in the effluent from the addition reaction zone, are fed to the fluorination reaction zone. It is noted that complete fluorination of all compounds of the formula $CH_2XCFXCX_2F$ results in formation of HFC-236cb.

It is normally desirable to completely fluorinate the HCFC-234 isomers of the formula $CH_2XCFXCX_2F$ to form the HFC-236cb with high selectivity. Accordingly, the molar ratio of HF to HCFC-234 isomers of the formula $CH_2XCFXCX_2F$ is typically from about 2:1 to about 50:1, preferably from about 4:1 to about 20:1.

The fluorination of HCFC-234 may be carried out in batch, semi-continuous, or continuous modes. In the batch mode, liquid HCFC-234 and hydrogen fluoride are combined in an autoclave or other suitable reaction vessel and heated to the desired temperature. Preferably, the process of the invention is carried out by feeding liquid HCFC-234 to a reactor containing HF held at the desired reaction temperature. Alternatively, HF may be fed to a reactor containing HCFC-234.

In another embodiment of the fluorination, both HF and HCFC-234 may be fed concurrently in the desired stoichiometric ratio (about 2:1) to a reactor containing a mixture including HCFC-234 and excess HF.

Temperatures suitable for reacting HCFC-234 with HF in the liquid phase are typically from about 70° C. to about 170° C. Higher temperatures typically result in higher conversions of HCFC-234.

The pressure of the fluorination in liquid phase embodiments is usually taken to be the autogenous pressure of the system at the reaction temperature. The pressure of the system increases as hydrogen chloride is formed by replacement of chlorine substituents for fluorine substituents in the HCFC-234 starting material. In a continuous process it is possible to set the pressure of the reactor in such a way that the HCl liberated by the reaction is vented from the reactor. Of note are embodiments in which the HFC-236cb product is allowed to vent from the reactor as it is produced in the form of its HF azeotrope. The HF azeotrope of HFC-236cb is disclosed in U.S. Patent Application No. 60/842,550 (corresponding to attorney docket no. FL-1253) filed Sep. 5, 2006 (the teachings of which are incorporated herein by reference). U.S. Pat. Application No. 60/842,550 is the priority document for International Patent Application No. PCT/US2007/ 19313.

Suitable catalysts which may be used for the fluorination when carried out in the liquid phase include $AlF_3$, $BF_3$, $FeX_3$ where X is selected from the group consisting of Cl and F, $FeX_3$ supported on carbon, $SbCl_{3-x}F_x$ (x=0 to 3), $AsF_3$, $MCl_{5-y}F_y$ (M=Sb, Nb, Ta, Mo; x=0 to 5), $M'Cl_{4-z}F_z$ (M'=Sn, Ti, Zr, Hf; z=0 to 4).

In yet another embodiment, HCFC-234 and HF may be fed to a heated tubular reactor containing a fluorination catalyst.

Temperatures suitable for reacting HCFC-234 with HF in the vapor phase are typically from about 150° C. to about 400° C.

The pressure of the fluorination reaction in vapor phase embodiments is not critical and may be atmospheric or superatmospheric. The pressure in the reactor should be sufficient to maintain HF, the organic reactants, intermediates, and product components in the vapor state at the operating temperature. Reactor pressures of about 5 atmospheres to about 30 atmospheres may be advantageously employed to facilitate separation of HCl from other reaction products in subsequent separation steps which are commonly used in the art (e.g., distillation).

Suitable catalyst which may be used for the fluorination of HCFC-234 when carried out in the vapor phase include metals (including elemental metals, metal oxides and/or other metal salts); alumina; fluorided alumina; aluminum fluoride; metals on alumina; metals on aluminum fluoride; magnesium fluoride on aluminum fluoride; metals on fluorided alumina; alumina on carbon; aluminum fluoride on carbon; fluorided alumina on carbon; metals on carbon; chromium catalysts (e.g., $Cr_2O_3$ by itself or with other metals such as Mg, Zn, Fe, Co, Ni, Cu); mixtures of metals, aluminum fluoride, and graphite; and chromium-magnesium optionally on graphite. Preferably when used on a support, the total metal content of the catalyst will be from about 0.1 to 20 percent by weight; typically from about 0.1 to 10 percent by weight.

Fluorided alumina and aluminum fluoride can be prepared as described in U.S. Pat. No. 4,902,838. Metals on aluminum fluoride and metals on fluorided alumina can be prepared by procedures described in U.S. Pat. No. 4,766,260.

Of note are chromium-containing catalysts (e.g., $Cr_2O_3$ by itself or with other metals such as Mg, Zn, Fe, Co, Ni, Cu in the form of metal halides or other compounds supported on $Cr_2O_3$); and mixtures of chromium-magnesium compounds (including metal oxides, metal halides, and/or other metal salts) optionally on graphite. Preferred vapor phase fluorination catalysts comprise trivalent chromium. Catalysts comprising chromium are well known in the art (see e.g., U.S. Pat. No. 5,036,036). Chromium supported on alumina can be prepared as described in U.S. Pat. No. 3,541,165. Chromium supported on carbon can be prepared as described in U.S. Pat. No. 3,632,834. Catalysts comprising chromium and magnesium may be prepared as described in U.S. Pat. No. 6,288, 293.

Of particular note are $Cr_2O_3$ prepared by pyrolysis of $(NH_4)_2Cr_2O_7$, $Cr_2O_3$ having a surface area greater than about 200 m²/g, and $Cr_2O_3$ prepared by pyrolysis of $(NH_4)_2Cr_2O_7$ or having a surface area greater than about 200 m²/g which is pre-treated with a vaporizable fluorine-containing compound such as HF or a fluorocarbon such as $CCl_3F$. These pre-treated catalysts are most preferred.

The $Cr_2O_3$ catalyst prepared by the pyrolysis of ammonium dichromate can be prepared by any method known to the art including those disclosed in U.S. Pat. Nos. 4,843,181 and 5,036,036 which are hereby incorporated herein by reference. Other $Cr_2O_3$ catalysts which may be used in (a) include catalysts having a surface area greater than about 200 m²/g, some of which are commercially available.

Also of note are cobalt-substituted alpha-chromium oxide compositions disclosed in U.S. patent application Ser. No. 10/523,228, filed Aug. 21, 2003, nickel-substituted alpha-chromium oxide compositions disclosed in U.S. patent application Ser. No. 10/523,226, filed Aug. 21, 2003, and copper-substituted alpha-chromium oxide compositions disclosed in U.S. Patent Application No. 60/706,159, filed Aug. 5, 2005. The teachings of these disclosures are incorporated by reference.

Generally, the fluorination catalysts (e.g., $Cr_2O_3$) will be pretreated with HF. This pretreatment can be accomplished by placing the catalyst in a suitable container which can be the reactor to be used to perform the fluorination reaction, and thereafter, passing HF over the pre-dried catalyst so as to partially saturate the catalyst with HF. This is conveniently carried out by passing HF over the catalyst for a period of time, for example, about 15 to 360 minutes at a temperature of, for example, about 200° C. to about 450° C. Nevertheless, this pretreatment is not essential.

The HFC-236cb produced as described above can be used to prepare HFC-1225ye. HFC-1225ye may exist as one of two configurational isomers, E or Z. HFC-1225ye as used herein refers to the isomers, E-HFC-1225ye (CAS Reg. No. [5595-10-8]) or Z-HFC-1225ye (CAS Reg. No. [5528-43-8]), as well as any combinations or mixtures of such isomers.

In one embodiment of the invention, the HFC-236cb is contacted with a dehydrofluorination catalyst in a reaction zone for time sufficient to convert at least a portion of the 236cb to HFC-1225ye. Suitable dehydrofluorination catalysts include chromium oxide (e.g., $Cr_2O_3$) and chromium oxyfluorides obtained by treating $Cr_2O_3$ with a fluorinating agent such as HF or $CCl_3F$. Suitable chromium oxide may be obtained commercially. The dehydrofluorination reaction may be conducted in a tubular reactor in the vapor phase at temperatures of from about 200° C. to about 500° C. The reaction pressures may be subatmospheric, atmospheric, or superatmospheric. Reaction times are generally in the range of about one second to 1000 seconds. Further details of this process are disclosed in U.S. Patent Application No. 60/830,939 filed Jul. 13, 2006, the teachings of which are incorporated by reference.

In another embodiment of this invention, the HFC-236cb is contacted with a base as disclosed in U.S. Patent Application No. 60/842,425 (corresponding to attorney docket no. FL-1267) filed Sep. 5, 2006 (the teachings of which are incorporated by reference). U.S. Patent Application No. 60/842,425 is the priority document for International Patent Application No. PCT/US2007/_____.

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific Examples are to be construed as merely illustrative, and do not constrain the remainder of the disclosure in any way whatsoever.

EXAMPLES

| Legend: | |
|---|---|
| HFC-236cb | $CH_2FC_2F_5$ |
| HFC-236ea | $CHF_2CHFCF_3$ |
| Z-HFC-1225ye | $Z\text{-}CHF\!\!=\!\!CFCF_3$ |
| E-HFC-1225ye | $E\text{-}CHF\!\!=\!\!CFCF_3$ |
| HCFC-226ca | $CHClFCF_2CF_3$ |

| -continued | |
|---|---|
| Legend: | |
| HFC-227ca | $CHF_2CF_2CF_3$ |
| HCFC-234cc | $CH_2ClCF_2CClF_2$ |
| HCFC-235cb | $CH_2ClC_2F_5$ |
| HCFC-235cc | $CH_2FCF_2CClF_2$ |

Example 1

Reaction of Chlorofluoromethane and Chlorotrifluoroethylene

Example 1 demonstrates the reaction of HCFC-31 with CTFE to produce HCFC-234cc ($CH_2ClCF_2CClF_2$). A 400 mL Hastelloy™ C shaker tube was charged with $AlCl_3$ (1.6 g, 0.012 mole) and 20 g of $CHCl_2CF_3$ (HCFC-123). The tube was cooled to −78° C., evacuated, and purged with nitrogen three times. HCFC-31 (18.0 g, 0.263 mole) and CTFE (25.0 g, 0.215 mole) were condensed into the tube. The cold tube was placed in the barricade and the temperature brought to 51° C. The tube was held at 50-52° C. for six hours; the pressure decreased steadily from 100 psig (kPa) to 65 psig (kPa) at the end of the run. The resulting product weighed 39.5 g. Analysis of the product by $^1H$ NMR indicated the major products as shown in Table 1.

TABLE 1

| Component | GC Area % | Mole % |
|---|---|---|
| $CHCl_2CF3$ | 29.4 | 31.1 |
| $CH_2Cl_2$ | 11.1 | 30.0 |
| $CH_2ClCF_2CClF_2$ | 25.6 | 22.3 |

Example 2

Fluorination of HCFC-234cc

Fluorination of HFC-234cc is illustrated by the following prophetic example based largely on the analogous teachings of U.S. Pat. No. 4,851,595, incorporated herein by reference.

A Hastelloy® reactor is charged with HCFC-234cc (50 g, 0.27 mole) and antimony pentafluoride (176 g, 0.81 mole). This mixture is then heated and stirred at 100° C. for about 3 hours. Under these conditions the conversion of HCFC-234cc is at least about 30% and the converted products is primarily HFC-236cb.

Additional disclosure of the fluorination of HCFC-234cc can be found in U.S. Pat. No. 5,264,639, incorporated herein by reference.

Example 3

Dehydrofluorination of HFC-236cb

Dehydrofluoination of HFC-236cb is illustrated by the following prophetic example based largely on the teachings of U.S. Patent Application No. 60/830,939, filed Jul. 13, 2006 and International Application No. PCT/US2007/015751, filed Jul. 11, 2007, both incorporated herein by reference.

An Inconel™ tube (⅝ inch OD (1.59 cm)) is charged with chromium oxide pellets (5 cc, 7.18 g, 12-20 mesh (1.68-0.84 mm)). The chromium oxide is prepared by the pyrolysis of ammonium dichromate as described in U.S. Pat. No. 5,036,036, herein incorporated by reference. The chromium oxide has an alpha-$Cr_2O_3$ structure and contains less than about 100 ppm of alkali metals; the surface area is about 40-60 $m^2$/gm.

The chromium oxide is activated according to the following sequence: (1) heating to 200° C. for 15 minutes under a purge of $N_2$ (50 sccm, $8.33\times10^{-7}$ $m^3$/s) and then increasing the temperature to 400° C. over 30 minutes, (2) lowering the temperature to 300° C. for 35 minutes, (3) flowing $N_2$ (35 sccm, $5.83\times10^{-7}$ $m^3$/s) and HF (12 sccm, $2.00\times10^{-7}$ $m^3$/s) for 35 minutes and then increasing the temperature to 350° C. for 60 minutes, followed by 375° C. for 90 minutes, followed by 400° C. for 30 minutes, and finally 425° C. for 40 minutes, (4) while maintaining the temperature at 425° C., the flow of $N_2$ is reduced to 25 sccm ($4.17\times10^{-7}$ $m^3$/s) and HF is increased to 20 sccm ($3.33\times10^{-7}$ $m^3$/s) for 20 minutes, (5) while maintaining the temperature at 425° C., the flow of $N_2$ is reduced to 15 sccm ($2.50\times10^{-7}$ $m^3$/s) and HF is increased to 28 sccm ($4.67\times10^{-7}$ $m^3$/s) for 20 minutes, (6) while maintaining the temperature at 425° C., the flow of $N_2$ is reduced to 5 sccm ($8.33\times10^{-8}$ $m^3$/s) and HF is increased to 36 sccm ($6.00\times10^{-7}$ $m^3$/s) for 20 minutes. The flow of HF is then stopped and the reactor tube cooled to about 350° C. under a nitrogen flow.

HFC-236cb and nitrogen are then passed through the catalyst bed at about 21 sccm ($3.5\times10^{-7}$ $m^3$/s) and 5.0 sccm ($8.33\times10^{-8}$ $m^3$/s), respectively; contact time of the HFC-236cb with the catalyst is about 30 seconds. Analysis of the reactor effluent shows approximately 60 GC area % HFC-236cb, 32 GC area % Z-HFC-1225ye, 4 GC area % E-HFC-1225ye, and 4 GC area % HFC-236ea.

The catalyst is heated to 200° C. for 15 minutes under a purge of $N_2$ (50 sccm, $8.33\times10^{-7}$ $m^3$/s). Then the temperature is raised to 325° C. for 10 minutes, to 400° C. for 20 minutes, and lowered to 300° C. for 35 minutes. The temperature is then raised to 325° C. for 60 minutes while flowing $N_2$ (35 sccm, $5.83\times10^{-7}$ $m^3$/s) and HF (12 sccm, $2.00\times10^{-7}$ $m^3$/s) for 35 minutes. While maintaining this flow, the temperature is raised to 350° C. for 60 minutes, 375° C. for 90 minutes, 400° C. for 30 minutes, and 425° C. for 40 minutes. The flow of $N_2$ is reduced to 25 sccm ($4.17\times10^{-7}$ $m^3$/s) and HF raised to 20 sccm ($3.33\times10^{-7}$ $m^3$/s) for 20 minutes. Then the flow of $N_2$ is reduced to 15 sccm ($2.50\times10^{-7}$ $m^3$/s) and HF raised to 28 sccm ($4.67\times10^{-7}$ $m^3$/s) for 20 minutes. Then the flow of $N_2$ is reduced to 5 sccm ($8.33\times10^{-8}$ $m^3$/s) and HF raised to 36 sccm ($6.00\times10^{-7}$ $m^3$/s) for 20 minutes.

The invention claimed is:

1. A process for making $CH_2ClCF_2CClF_2$, comprising:
reacting $CH_2ClF$ with $CClF=CF_2$ in an addition reaction zone in the presence of a catalytically effective amount of an aluminum halide composition having a bulk formula of $AlCl_xBr_yF_{3-x-y}$ wherein the average value of x is 0 to 3, the average value of y is 0 to 3−x, provided that the average values of x and y are not both 0.

2. A process for making $CH_2FCF_2CF_3$ comprising:
reacting $CH_2ClCF_2CClF_2$ produced by the process of claim 1 with HF in a fluorination reaction zone in the presence of a fluorination catalyst to produce a product comprising $CH_2FCF_2CF_3$.

3. The process of claim 2 wherein $CH_2ClCF_2CClF_2$ and other compounds of the formula $CH_2XCFXCX_2F$, wherein two X are Cl and the other two X are F that are present in the effluent from the addition reaction zone, are fed to the fluorination reaction zone.

4. A process for making $CHF=CFCF_3$, comprising:
dehydrofluorinating $CH_2FCF_2CF_3$ produced by the process of claim 2 to form $CHF=CFCF_3$.

5. The process of claim 4 wherein $CH_2ClCF_2CClF_2$ and other compounds of the formula $CH_2XCFXCX_2F$, wherein two X are Cl and the other two X are F that are present in the effluent from the addition reaction zone, are fed to the fluorination reaction zone.

* * * * *